United States Patent [19]
Perren et al.

[11] Patent Number: 5,019,078
[45] Date of Patent: May 28, 1991

[54] BONE SCREW

[75] Inventors: Stephen M. Perren; Robert Frigg, both of Davos-Dorf; Paul Gisin, Waldenburg; Robert Mathys, Jr., Bettlach, all of Switzerland

[73] Assignee: Synthes (U.S.A.), Paoli, Pa.

[21] Appl. No.: 437,581

[22] Filed: Nov. 17, 1989

[30] Foreign Application Priority Data

Nov. 17, 1988 [CH] Switzerland .................. 04263/88

[51] Int. Cl.$^5$ .................................................. A61B 17/58
[52] U.S. Cl. .................................................. 606/61; 606/73
[58] Field of Search .................. 606/60, 61, 72, 73

[56] References Cited

U.S. PATENT DOCUMENTS

| 4,463,753 | 8/1984 | Gustilo | 606/73 |
| 4,468,200 | 8/1984 | Münch | 606/73 X |
| 4,524,765 | 6/1985 | de Zbikowski | 606/73 X |
| 4,913,134 | 4/1990 | Luque | 606/73 X |

Primary Examiner—Robert A. Hafer
Assistant Examiner—Kevin G. Rooney
Attorney, Agent, or Firm—Davis Hoxie Faithfull & Hapgood

[57] ABSTRACT

A bone screw has a smooth shaft segment, a threaded segment and a tapered transition segment between the shaft and the threaded segment.

13 Claims, 1 Drawing Sheet

BONE SCREW

FIELD OF THE INVENTION

This invention relates to bone screws and particularly to bone screws of the so-called Schanz type. Such screws have a screw head, a smooth shank segment, and a threaded segment.

BACKGROUND OF THE INVENTION

With conventional designs of Schanz screws, with any additional load on the screw in a radial direction, the driving pressure is reinforced on one side while being relieved on the other because of the absence of pre-stress. This can lead to a loosening of the screw and subsequent bone resorption. (cf. S. M. Perren, R. Ganz, and A. Ruter, *Med. Orthop. Technik*, Heft 1/75, 95 Jahrg. (1975) pp.6–10). In addition, with conventional Schanz screws, two drilling procedures are necessary, one with a drill for the minor diameter $d_1$ and the other with a drill for the major diameter $d_2$. If one tries to simplify the procedure by forming a single, undersized hole, micro and macro fractures occur in the bone material.

In conventional Schanz screws the transition between the shank and thread segments, both of which have the same outside diameter, is formed as a channel that either punches the bone material along its leading edge or cuts it along its back edge. There is not merely a radial spreading of the bone material.

SUMMARY OF THE INVENTION

In accordance with the invention, a bone screw is provided which can be inserted with only one drilling procedure, under radial compression of the bone material, without bone injury, and which retains the radial driving pressure along with the entire surface even under additional functional loads.

Such results are obtained in accordance with the invention by means of a bone screw having a head, a smooth shaft segment having a diameter $D_1$, adjacent said head, a threaded segment, and a transition segment between the shaft segment and the threaded segment, said transition segment tapering from a diameter $D_1$ adjacent the shaft segment to a diameter $D_2$ adjacent the threaded segment, the ratio $$\frac{D_1 - D_2}{D_2}$$

being less than the breaking elongation of the bone.

BRIEF DESCRIPTION OF THE DRAWINGS

The invention will be further described with reference to the accompanying drawings in which.

DETAILED DESCRIPTION OF THE INVENTION

Figure 1:
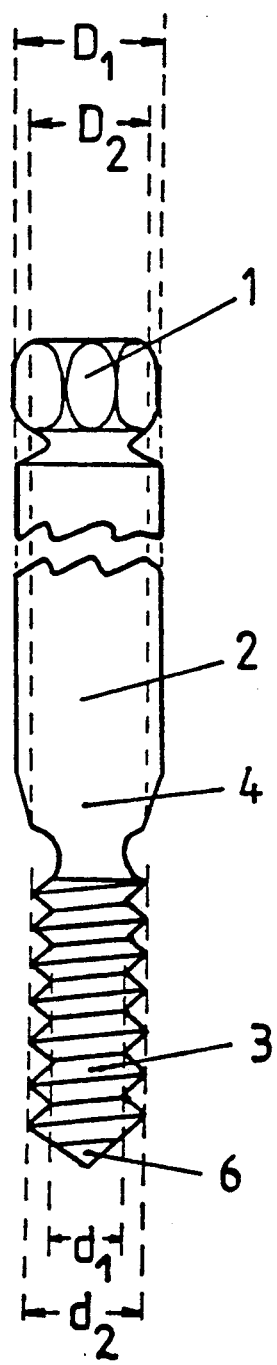
FIG. 1 is a view in elevation, partly broken away, of a bone screw in accordance with the invention.

Referring to FIG. 1, a bone screw according to the invention comprises a screw head 1, a smooth shaft segment 2, having a diameter $D_1$ and a threaded segment 3 having a minor diameter $d_1$ and a major diameter $d_2$. Between the shaft segment 2 and the threaded segment 3 is located a tapered transition segment 4. In the embodiment shown in FIG. 1 the transition segment is conically shaped and narrows continuously from diameter $D_1$ to a lesser diameter $D_2$. The free end 6 of the threaded segment 3 is constructed as an automatically expanding screw tip (Trocar tip).

The breaking elongation of a bone will normally be about 2–3%. The size of the transition segment should be selected so that the ratio $$\frac{D_1 - D_2}{D_2}$$

is less than the breaking elongation of the bone, say from about 0.001 to about 0.040 preferably between about 0.010 and 0.030. This range will result in optimum compression of bone material.

The diameter $D_2$ at the narrower end of the transition segment should advantageously correspond to the major diameter $d_2$ of the threaded segment to guarantee sufficient compression of the bone material by the smooth shaft segment.

The threaded segment is preferably dimensioned so that the ratio between the minor and major diameter, $d_1/d_2$ is between about 0.80 and about 0.89, preferable between about 0.83 and about 0.86.

To prevent simultaneous action by the threaded segment on the rear corticalis and by the transition segment on the front corticalis, which would lead to loss of control when the bone screw is screwed in, it is advantageous to position the transition segment at a distance of from about 11 to about 15 mm, preferably from about 12 to about 14 mm from the free end of the threaded segment, i.e., the end remote from the transition segment.

In a specific example of a screw according to FIG. 1 the shaft segment may have a diameter $D_1$ of 4.5 mm, and the threaded segment may have major and minor diameters of 4.4 mm and 3.8 mm, respectively. The end of the transition segment has a diameter, $D_2$, equal to 4.4 mm, the major diameter $d_2$ of the thread. The distance between the transition segment 4 and the tip of segment 3 is about 13 mm.

Figure 2:
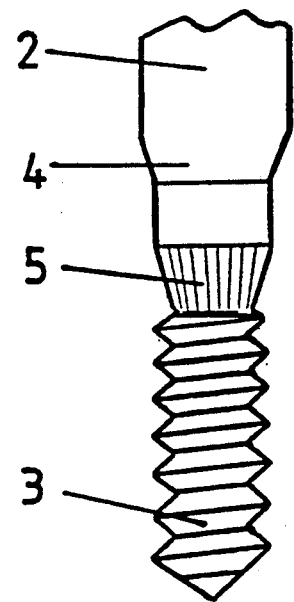
FIG. 2 is a view in elevation of a fragment of a modified version of the bone screw of FIG. 1.

In FIG. 2 there is shown a modification of a screw according to the invention in which a milling segment 5 having straight longitudinal lands and groves is interposed between the transition segment 4, which is constructed as a shoulder, and the threaded segment 3.

Figure 3:
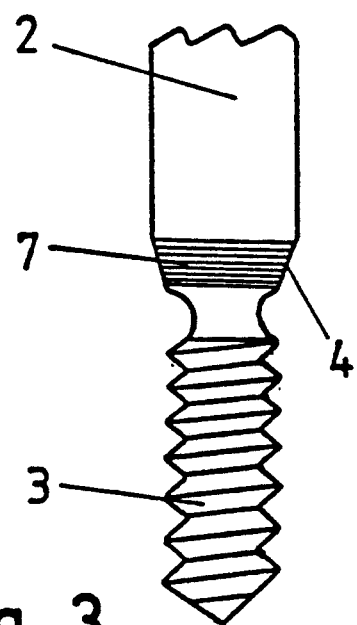
FIG. 3 is a view in elevation of a fragment of a differently modified version of the bone screw of FIG. 1.

A further embodiment of the invention is shown in FIG. 3. There the transition segment 4 is formed with a shallow thread. This will ensure further advance of the screw into the bone, even before the rear cortical wall is reached.

What is claimed is:

1. A bone screw having a head, a smooth shaft segment having a diameter $D_1$ adjacent said head, a threaded segment and a transition segment between the smooth shaft segment and the threaded segment, said transition segment tapering from a diameter $D_1$ adjacent said smooth shaft segment to a lesser diameter $D_2$ adjacent said threaded segment, the ratio $$\frac{D_1 - D_2}{D_2}$$

being between 0.001 and 0.040.

2. The bone screw claimed in claim 1, wherein the ratio is between 0.010 and 0.030.

3. The bone screw claimed in claim 1, wherein the transition segment has a self-cutting thread.

4. The bone screw claimed in claim 1, wherein the transition segment narrows continuously from $D_1$ to $D_2$.

5. The bone screw claimed in claim 1, wherein the transition segment has a shallow thread.

6. The bone screw claimed in claim 1 and comprising a milling segment between the threaded segment and the transition segment.

7. The bone screw claimed in claim 1, wherein the threaded segment has a minor diameter $d_1$ and a major diameter $d_2$, the ratio $d_1/d_2$ being between about 0.80 and 0.89.

8. The bone screw claimed in claim 7, wherein the ratio is between about 0.83 and 0.86.

9. The bone screw claimed in claim 1, wherein the threaded segment has an automatically expanding screw tip at its end remote from the transition segment.

10. The bone screw claimed in claim 9, wherein the tip is a Trocar tip.

11. The bone screw claimed in claim 1, wherein the transition segment is from about 11 to about 15 mm from the remote end of the threaded segment.

12. The bone screw claimed in claim 11, wherein the transition segment is from about 12 to about 14 mm from the remote end of the threaded segment.

13. The bone screw claimed in claim 1, wherein the tip of the threaded segment has a corkscrew shape.

* * * * *